United States Patent [19]

Anninos et al.

[11] Patent Number: 5,453,072

[45] Date of Patent: Sep. 26, 1995

[54] ELECTRONIC APPARATUS FOR TREATING EPILEPTIC INDIVIDUALS

[76] Inventors: Photios Anninos, 20 Ellispontou St., Alexandroupolis; Nicolaos Tsagas, L. Thrakos 3, Xanthi, both of Greece

[21] Appl. No.: 867,201

[22] PCT Filed: Oct. 11, 1990

[86] PCT No.: PCT/GR90/00002

§ 371 Date: Jun. 30, 1992

§ 102(e) Date: Jun. 30, 1992

[87] PCT Pub. No.: WO91/06341

PCT Pub. Date: May 16, 1991

[30] Foreign Application Priority Data

Oct. 31, 1989 [GR] Greece .................. 890100705

[51] Int. Cl.$^6$ .................. A61N 1/00; A61N 2/04
[52] U.S. Cl. .................. 600/9
[58] Field of Search .................. 600/9–15; 128/653.1; 324/244, 245

[56] References Cited

U.S. PATENT DOCUMENTS 4,066,065  1/1978  Kraus .................. 600/13

FOREIGN PATENT DOCUMENTS

| 0084019 | 7/1983 | European Pat. Off. . |
| 0099734 | 2/1984 | European Pat. Off. . |
| 2370483 | 6/1978 | France . |
| 2707574 | 8/1978 | Germany . |

OTHER PUBLICATIONS

Physics Today—vol. 39, No. 3, Mar. 1986, New York US pp. 36–44; John Clarks: "SQUIDs, brains and gravity waves" see pp. 41–42.

Primary Examiner—William E. Kamm
Assistant Examiner—John P. Lacyk
Attorney, Agent, or Firm—Dowell & Dowell

[57] ABSTRACT

The invention is an electronic device for smoothing of dysfunctions of the central nervous system in conjunction with the use of a biomagnetometer SQUID. The device includes one generator of alternating low voltage which produces a frequency from 2 Hz to 7 Hz, and which supplies a number of selected coils of one group which consists of similar rows of coils, or a plurality of groups of similar coils arranged in rows. The device may include plural generators of alternating low voltage which each produces a frequency from 2 Hz to 7 Hz and which supply simultaneously a number of selected coils of one or more groups of similar coils arranged in rows.

19 Claims, 3 Drawing Sheets

ELECTRONIC APPARATUS FOR TREATING EPILEPTIC INDIVIDUALS

BACKGROUND OF THE INVENTION

The invention is an electronic device for smoothing of central nervous system dysfunctions in conjunction with the use of a biomagnetometer SQUID.

The electronic device comprises a generator of low alternating voltage and frequency which can produce a frequency from 2 Hz to 7 Hz, and a defined number of coils of one or more groups of similar coils, in order to produce alternating magnetic fields of defined magnetic field intensity. The device may optionally comprise a plurality of generators of alternating voltage and low frequency which can each produce a frequency from 2 to 7 Hz, and which can supply simultaneously a defined number of coils in order to produce alternating magnetic fields. The pulse of the alternating voltage can have a square, triangular, sinusoidal or saw-like form. Analogous pulse forms can have alternating magnetic fields which are produced by the coils, the ends of which are connected with the generator output. The number of coils and the cross-section of the coil turns, as well as the shape and composition of the cores, can be varied.

The magnetic fields which are produced simultaneously from the coils are parallel to the alternating magnetic fields which are emitted from the brain epileptic foci. In addition, the powers and frequencies of the emitted magnetic fields from the coils are of the same order of magnitude as those which are emitted from the epileptic foci. The device is useful to smooth epileptic convulsions in epileptic patients receiving anticonvulsion medication, yet who continue to have seizures. The time required for smoothing varies from patient to patient, and depends on the size of the epileptic foci. The smoothing can be repeated by a patient having a personal device, which can be calibrated with the use of the biomagnetometer SQUID which gives the epileptic foci, and any other brain dysfunction, characteristics. Patients can avoid any side effects because the applied magnetic fields are smaller than the earth's magnetic field. In contrast, side effects can occur with the different anticonvulsive drugs and the different methods of the known diagnostic techniques.

Before the electronic device is used, first the epileptic foci must be localized with the use of the SQUID. Prior research work has been published by the inventors P. A. Anninos and N. F. Tsagas: *Brain Research Bulletin*, Vol. 16, 1986; and *International Journal of Neuroscience*, Vol. 37, 1987. The known methods have used anticonvulsive drugs for smoothing of epileptic seizures for general and focal epilepsy, but without achieving the final cancellation of epileptic foci. Final cancellation of epileptic foci can be achieved either with neurosurgery or with the use of a laser, but the disadvantage of these two cures is that they can cause other brain dysfunctions. To avoid surgery, most patients prefer the drug treatment which only temporarily inhibits the epileptic seizures.

Other methods also apply instantly strong magnetic fields of the order of $10^5$ Gauss which cause side effects. The present invention overcomes these disadvantages because it solves the problem of smoothing the epileptic foci or other dysfunctions of the central nervous system without the use of the known invasive methods. It is safe because the applied alternating magnetic fields are of small frequency (2 to 7 Hz) and small intensity ($10^{-4}$ to $10^{-8}$ Gauss), which are $1/10^4$ or $1/10^8$ of the intensity of the earth's magnetic field. The duration of the smoothing treatment is only of the order of several minutes every time the device is applied to the epileptic foci. The smoothing treatment lasts several days or months, and the patient can alone repeat the treatment as needed when he feels or senses (by smell, taste, etc.) certain characteristic signs which tell him that he is going to have seizures.

The apparatus in accordance with the invention comprises one generator which produces an alternating voltage, a given frequency from 2 to 7 Hz, and which supplies a defined number of selected coils to produce alternating magnetic fields of defined intensity. The device may optionally comprise a plurality of generators that each can produce an alternating voltage, a low frequency from 2 Hz to 7 Hz, and which supply simultaneously a defined number of selected coils to produce alternating magnetic fields of definite intensity. The form of the alternating magnetic fields which are produced from the coils, the ends of which are connected with the output of the generator, is square wave (symmetrical or non-symmetrical), triangular, sinusoidal or saw-like. The number of turns and the cross-section of the coils, as well as the shape and the composition of the cores (plastic, ferrite and other materials of suitable magnetic permeability) can vary. The produced alternating magnetic fields are parallel to the alternating magnetic fields which are emitted from the neuronal generators of the epileptic foci. That is, the surface of the coils is applied simultaneously and parallel to the projected epileptic foci on the skull, or at another part of the central nervous system. The power and the frequency of the magnetic field of the coils are of the same order of magnitude as the magnetic fields which are emitted from the epileptic foci. The precise position of the epileptic foci, the intensity and the frequency of the magnetic fields which are emitted from the epileptic foci, and which are specific for each patient, are defined precisely with the use of the biomagnetometer SQUID. The use of SQUID is described in detail in the above-mentioned publications.

Advantages of the invention are fast, painless and non-invasive smoothing of the epileptic foci and the effective reduction of epileptic seizures. Furthermore, patients can perform their own smoothing with the use of the electronic device of the present invention.

BRIEF DESCRIPTION OF THE DRAWINGS

Embodiments of the present invention are described below with reference to the accompanying drawing figures.

DETAILED DESCRIPTION OF THE PREFERRED EMBODIMENTS

Figure 1:
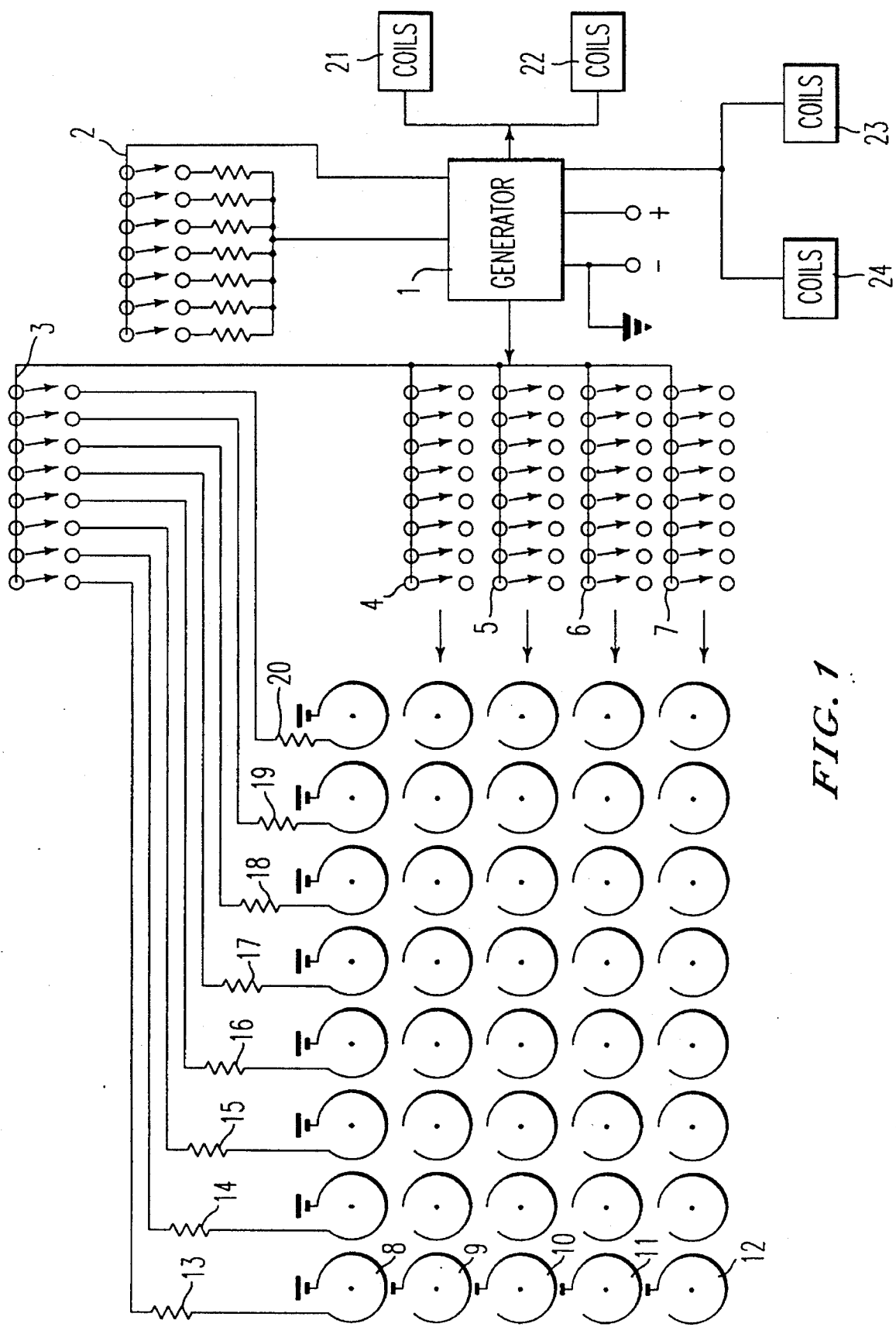
FIG. 1 illustrates an embodiment of the device according to the invention which comprises a generator (1) of alternating low voltage and frequency which can produce a defined frequency from 2 Hz to 7 Hz, a switch (2) for selecting the frequency, switches (3, 4, 5, 6, 7) for selecting the coils to which to supply the selected frequency, and of one or more groups of coils arranged in similar rows.

FIG. 1 illustrates an embodiment of an electronic device in accordance with the invention which can produce alternating magnetic fields for smoothing dysfunction of the central nervous system. The device comprises a generator (1) of alternating low voltage which can produce frequencies of 2 to 7 Hz, a switch (2) for selecting the operative frequency, switches (3, 4, 5, 6, 7) for selecting operative coils of one group of similar coils arranged in rows (8, 9, 10, 11, 12), or similar additional groups of coils (21, 22, 23, 24), resistors (13, 14, 15, 16, 17, 18, 19, 20) which connect the coils of the rows (8, 9, 10, 11, 12) with the switches (4, 5, 6, 7), and similar resistors (not shown) for the other groups of coils.

Figure 2:
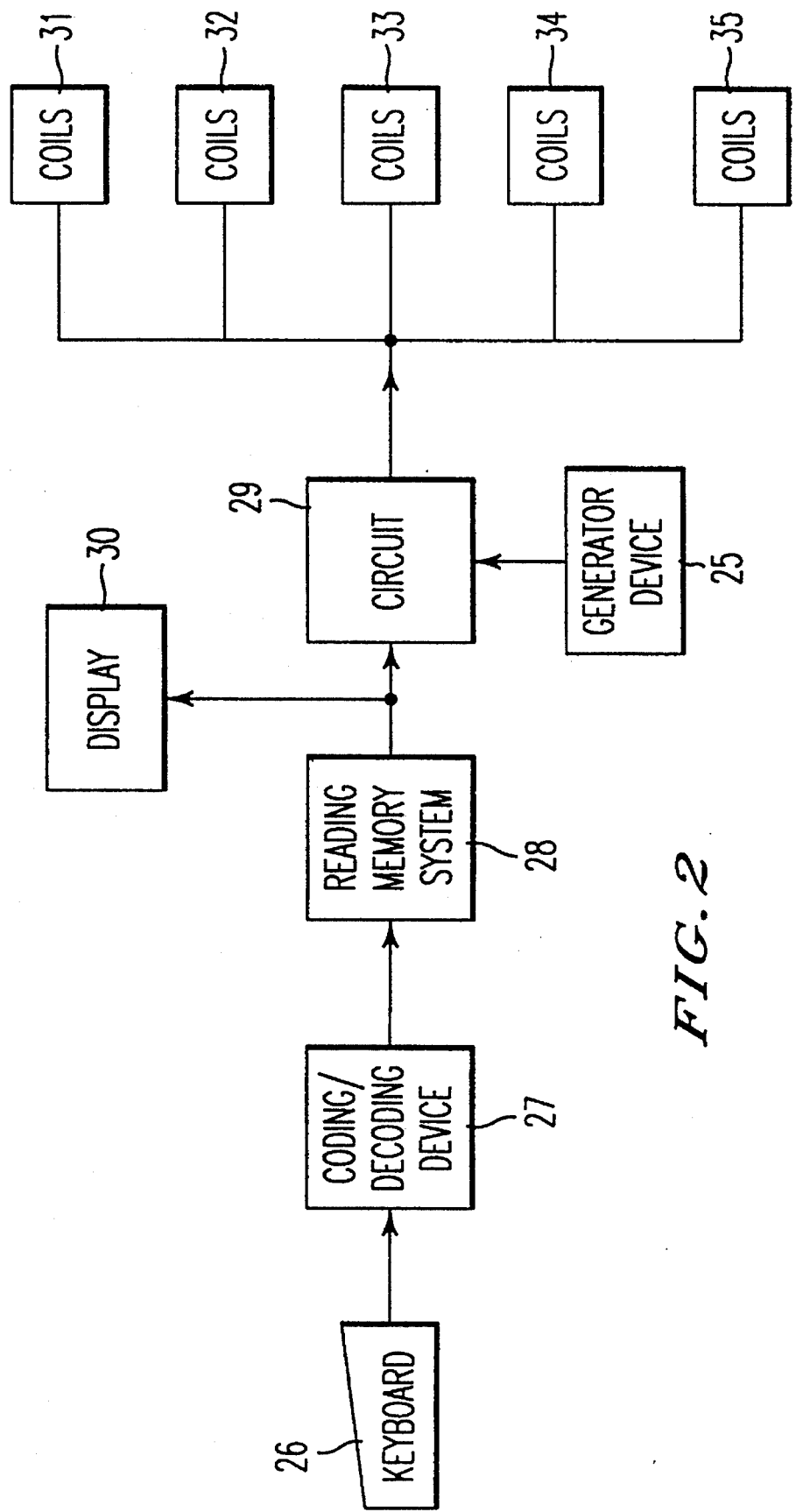
FIG. 2 illustrates another embodiment of the device according to the invention which comprises a plurality of generators (25) of alternating low voltage and frequency, which each can produce a frequency from 2 Hz to 7 Hz, a key board for selecting operative generators and coils, a code maker/decode maker of the key board, a memory reading system, a screen display, a combinatory circuit, and one or more groups of similar coils arranged in rows.

FIG. 2 illustrates another embodiment of an electronic device in accordance with the invention. The device comprises a generator device (25) including seven generators of low alternating voltage, which can each produce a frequency from 2 Hz to 7 Hz, a key board for selecting operative generators and coils (26), a code maker/decode maker (27), a reading memory system (28), a display screen (30), a combinatory circuit (29), and one group of similar coils arranged in rows (31), or similar additional groups of coils (32, 33, 34, 35). The coils of the different groups (31, 32, 33, 34, 35) are connected with the combinatory circuit (29) through resistors (not shown).

The coils have a small diameter of about one centimeter and are enclosed between two parallel plane surfaces such that the axis of the coils is perpendicular to the surfaces, which are located parallel to the projection of the epileptic foci on the skull. The perpendicular cross-section of the coils is substantially circular and the number of turns of the coils is relatively small. The coils comprise wire of small external cross-section and materials having good conductance (silver, copper and the like).

Figure 3A:
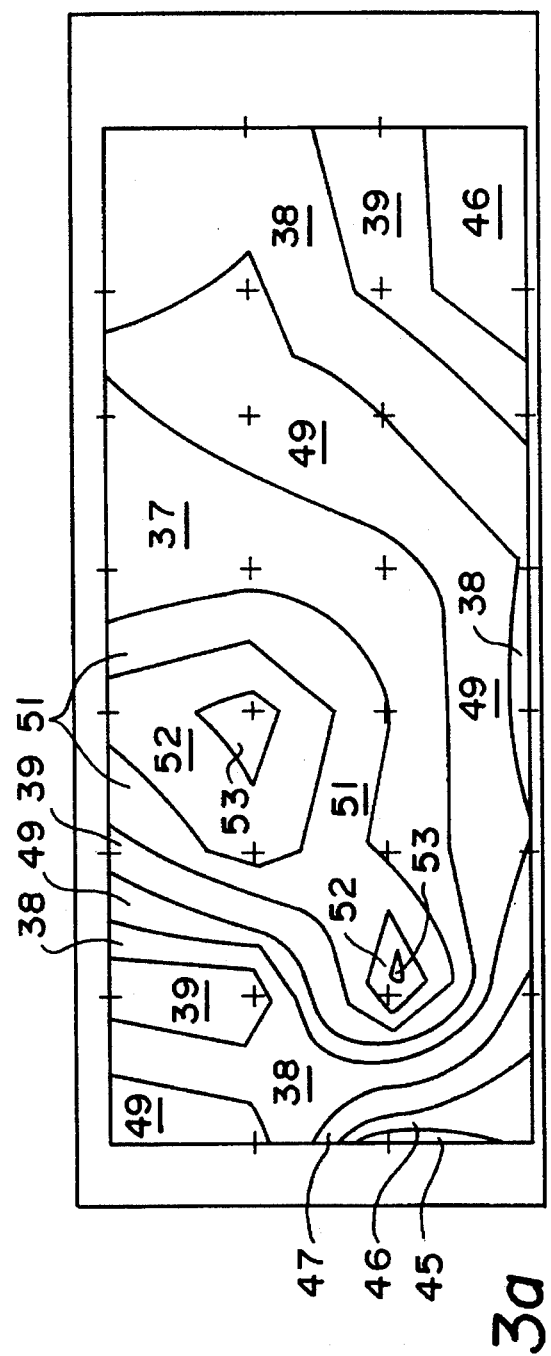
FIG. 3a illustrates an isospectral map which was produced from measurements made by a SQUID of the left temporal region of an epileptic patient before the smoothing treatment.

As illustrated in FIG. 3a, foci (36, 37, 38, 39) with corresponding power amplitudes above 2200 ft/√Hz, below 2200 ft/√Hz, and above 1800 ft/√Hz and below 1400 ft/√Hz, resulted from the isospectral mapping of the left temporal region of a patient with the use of the SQUID before smoothing. The coordinates of the epileptic foci (36, 37, 38, 39) are determined with the use of the SQUID. The power of the isospectral lines was also determined from mapping with the SQUID. The epileptic foci (36, 37, 38, 39) disappeared as shown in the corresponding region (40) after the application of the electronic device of the invention where the corresponding isospectral amplitudes are below 800 FT/√Hz (see FIG. 3b).

The effectiveness of the invention is based on the proper use of the biomagnetometer SQUID, at least for the first smoothing of the patient during which the first calibration of the device is performed. The SQUID has a probe which does not come in contact with skull, and it measures for each patient and for each hemisphere of the brain, 32 points having a distance of 1.5 cm, which is one-half of the SQUID sensor diameter in order to avoid magnetic overlapping between nearby points. These points form a matrix of rectangular shape and are located around the reference points of a 10–20 international point system for electrode placement. The reference points are designated T3, T4, P3, P4, F3, F4 for the left or right temporal hemisphere, the left or right occipital hemisphere, and the left or right frontal brain region. The 32 points are located with a self-adhesive paper on a plastic hat which is located on the patient's head prior to the location of the reference points.

Figure 3B:
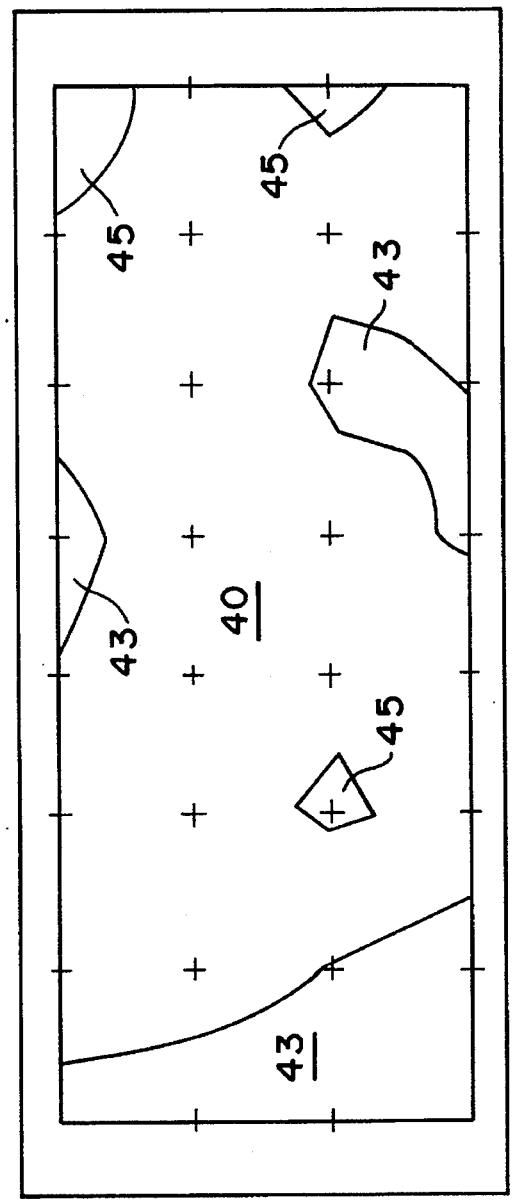
FIG. 3b illustrates a corresponding isospectral map produced from measurements of the same region of the brain of the same patient with the use of the SQUID after applying the electronic device of the present invention.

The 32 points are 1.5 cm from one another, and are located in perfectly defined positions in the skull with the use of the self-adhesive paper. This is achieved provided that the coordinates of the reference points have been defined, because by knowing the coordinates of the reference points, then also known are the coordinates of all 32 points, and, consequently, the coordinates of the epileptic foci (36, 37, 38). Next, the probe sensor of the SQUID is located 3 mm above each measuring point and 32 consecutive measurements of one second duration each are taken from each point with a sampling frequency of 256 Hz. The measurement of each point is analyzed using Fourier statistical analysis, and the amplitude distribution of the Fourier power spectrum in a given frequency, or in a given range of frequencies, is examined. Using electronic computers, all equal power spectra amplitudes for a given frequency or a given frequency range, are connected to obtain maps of isospectral amplitudes (FIGS. 3a, 3b). The following TABLE I gives the ISO-SA map region number and the corresponding MEG amplitude for FIGS. 3a and 3b.

TABLE I

| ISO-SA Map Region Number | MEG Amplitude (ft/√Hz) |
|---|---|
| 42 | <200 |
| 43 | <400 |
| 40 | <600 |
| 45 | <800 |
| 46 | <1000 |
| 39 | <1200 |
| 38 | <1400 |
| 49 | <1600 |
| 37 | <1800 |
| 51 | <2000 |
| 52 | <2200 |
| 36 | >2200 |

From these maps and from the power spectrum density are obtained results if there are epileptic foci (36, 37, 38) as well as the coordinates and the power of the epileptic foci. Finally, after the identification of the epileptic foci (36, 37, 38) with the use of spectral analysis, the frequency of the emitted field from the focus is found. The device is completely connected with the SQUID measurements because it is necessary for the calibration of the device of the invention. In other words the patient is not able alone to locate the device on his skull without the above information because it can disorganize other regions of the brain.

The epileptic foci (36, 37, 38, 39) with corresponding magnitudes which varied from 1200 ft/√Hz to above 2200 ft/√hz were reduced with the application of the modified electronic device of the invention to levels below 800 ft/√Hz (FIG. 3b).

We claim:

1. An electronic apparatus for treating an epileptic individual, having an epileptic focal point skull distribution, intensity and frequency as determined by a superconducting quantum interference device (SQUID), to inhibit seizure activity, the apparatus comprising:

generating means for generating an alternating low voltage and a frequency of from about 2 Hz to about 7 Hz; and emitting means for emitting a magnetic field to the skull of the epileptic individual of substantially the same distribution, intensity and frequency as the individual's epileptic focal points, said emitting means comprises a group of coils having a plurality of rows of coils, and each of the rows of coils includes a plurality of coils; and means for electrically connecting said generating means to said emitting means.

2. The apparatus of claim 1, wherein said emitting means comprises a plurality of groups of coils, each of the groups of coils having a plurality of rows of coils, and each of the rows of coils includes a plurality of coils.

3. The apparatus of claim 1, wherein each coil is enclosed between a pair of substantially parallel surfaces and has a central axis perpendicular to said parallel surfaces, said parallel surfaces being adapted to be positioned substantially parallel with respect to projections of epileptic focal points on the skull, in which position said magnetic field is substantially parallel to a magnetic field emitted from the epileptic focal points.

4. The apparatus of claim 2, wherein each coil is enclosed between a pair of substantially parallel surfaces and has a central axis perpendicular to said parallel surfaces, said parallel surfaces being adapted to be positioned substantially parallel with respect to projections of epileptic focal points on the skull, in which position said magnetic field is substantially parallel to a magnetic field emitted from the epileptic focal points.

5. The apparatus of claim 3, wherein each coil has a diameter of about 1 cm.

6. The apparatus of claim 4, wherein each coil has a diameter of about 1 cm.

7. The apparatus of claim 1, further comprising first switching means for selectively electrically connecting said generating means to said group of coils.

8. The apparatus of claim 2, further comprising second switching means for selectively electrically connecting said generating means to said plurality of groups of coils.

9. The apparatus of claim 1, wherein said generating means comprises a single generator.

10. The apparatus of claim 1, wherein said generating means comprises a plurality of generators, and each generator produces an alternating voltage and a frequency of from about 2 Hz to about 7 Hz.

11. The apparatus of claim 9, wherein said emitting means produces pulses selected from the group consisting of square pulses, triangular pulses, sinusoidal pulses and saw-like pulses.

12. The apparatus of claim 10, wherein said emitting means produces pulses selected from the group consisting of square pulses, triangular pulses, sinusoidal pulses and saw-like pulses.

13. The apparatus of claim 9, further comprising third switching means for selecting the frequency produced by said generating means.

14. An electronic apparatus for treating an epileptic individual, having an epileptic focal point skull coordinate distribution, intensity and frequency as determined by a superconducting quantum interference device (SQUID), to inhibit seizure activity, the apparatus comprising:

a plurality of generator means for generating an alternating voltage and a frequency of from about 2 Hz to about 7 Hz;

a plurality of groups of coil means for emitting a magnetic field to the skull of the epileptic individual, each of said groups of coil means including a plurality of coils; and connecting means for selectively electrically connecting the generator means and groups of coil means such that the selected coil means emit a magnetic field having substantially the same distribution, intensity and frequency as the individual's epileptic focal points.

15. The apparatus of claim 14, wherein said connecting means comprises a key board and a connecting circuit for electrically connecting the key board to the selected generator means and coil means.

16. The apparatus of claim 15, wherein said connecting means further comprises a coding device, a reading memory system and a display, being electrically connected to said key board.

17. The apparatus of claim 14, wherein each of the coil means is enclosed between a pair of substantially parallel surfaces and has a central axis perpendicular to said parallel surfaces, said parallel surfaces being adapted to be positioned substantially parallel with respect to projections of epileptic focal points on the skull, in which position said magnetic field is substantially parallel to a magnetic field emitted from the epileptic focal points.

18. The apparatus of claim 17, wherein each coil means has a diameter of about 1 cm.

19. The apparatus of claim 14, wherein each generator means produces an alternating voltage and a frequency of from about 2 Hz to about 7 Hz.

* * * * *